(12) United States Patent
Thuilliez et al.

(10) Patent No.: US 8,268,949 B2
(45) Date of Patent: Sep. 18, 2012

(54) BOROHYDRIDE METALLOCENE COMPLEX OF A LANTHANIDE, CATALYTIC SYSTEM INCLUDING THE SAID COMPLEX, POLYMERISATION METHOD USING SAME AND ETHYLENE/BUTADIENE COPOLYMER OBTAINED USING SAID METHOD

(75) Inventors: Julien Thuilliez, Clermont-Ferrand (FR); Christophe Boisson, Tramoyes (FR); Roger Spitz, Lyons (FR)

(73) Assignees: Michelin Recherche et Technique S.A., Granges-Paccot (CH); Total Petrochemicals France, Puteaux (FR); Centre National de la Recherche Scientifique, Paris (FR); Ecole Superieure de Chimie-Physique-Electronique de Lyon, Cedex (FR)

( * ) Notice: Subject to any disclaimer, the term of this patent is extended or adjusted under 35 U.S.C. 154(b) by 0 days.

(21) Appl. No.: 13/290,617

(22) Filed: Nov. 7, 2011

(65) Prior Publication Data
US 2012/0165492 A1    Jun. 28, 2012

Related U.S. Application Data

(62) Division of application No. 12/084,808, filed on Aug. 5, 2009, now Pat. No. 8,071,800.

(30) Foreign Application Priority Data

Nov. 9, 2005    (FR) ..................................... 05 11393

(51) Int. Cl.
C08F 236/06    (2006.01)
C08F 4/52    (2006.01)
(52) U.S. Cl. ........ 526/339; 526/134; 526/137; 526/160; 526/164; 526/943; 502/103; 502/152
(58) Field of Classification Search .................. 526/134, 526/137, 160, 164, 339, 943; 502/103, 152
See application file for complete search history.

(56) References Cited

U.S. PATENT DOCUMENTS 7,094,854 B2 *    8/2006    Monteil et al. ................. 526/339

OTHER PUBLICATIONS

A.V. Khvostov et al., "ansa-Ytterbocene (III) choloride and borohydride with a short bridge and bulky substituents: synthesis and crystal structures of [meso-(CH3)2Si[3-(CH3)3SiC5H3]2Yb(m2-C1)]2 and meso-(CH3)2Si[3-(CH3)    3SiC5H3]2Yb [m2-H)3BH](THF)", Journal of Organometallic Chemistry, vol. 589, pp. 222-225, 1999.

C. Qian et al., "The first example of a dinuclear anionic lanthanoidocene complex:[K(18-crown-6){(C13H8)CPh2(C5H4)Nd(BH4)2}]2.C4H802", Journal of Organometallic Chemistry, Elsevier-Sequoia S.A., vol. 626, No. 12, pp. 171-175, Apr. 30, 2001.
M. Visseaux et al., "Synthesis and X-ray structure of a borohydro metallocene of neodymium and its use as pre-catalyst in Nd/Mg dual-Component ethylene and isoprene polymerizations", Journal of Organometallic Chemistry, Elsevier-Sequoia S.A., vol. 691, pp. 86-92, Oct. 4, 2005.
Database WPI Derwent Publications Ltd., London, GB; 2001, Xp002447599, Database Accession No. 2001-398808.
A. V. Khvostov et al., "Synthesis and structural study of the ate-complex rac-(CH32C(C5H3-3-Si(CH3)3)2Yb(mu2-CI)2Li(Oet2)2 and the polymeric compound {rac-(CH3)2C(C5H3-3-Si(CH3)3)2Yb[(mu2-H)2B(mu-2-H)2]2Li(THF)2} {", Journal of Organometallic Chemistry, Elsevier-Sequoia S.A., vol. 564, No. 1-2, pp. 5-12, Aug. 14, 1998.
Qian et al., "Synthesis of diphenylmethylene bridged fluorenyl cyclopentadienyl lanthanocene complexes with Cs symmetry and crystal structures of the ate complexes [Li(thf)4] [LnC12{(C13H8) CPh2 (C5H4)}] and [Li(thf)4] [Ln(BH4)2{(C13H8) CPh2(C5H4)}] (Ln = Nd or La)", Journal of the Chemical Society, Dalton Transactions, Chemical Society pp. 3283-3287, 1999.
D. Barbier-Baudry et al., "Non-hindered ansasamarocenes, versatile catalysts for diene/olefin/polar monomer copoymerisations. What is really the active species?", Journal of Organometallic Chemistry, Elsevier-Sequoia S.A., vol. 647, No. 1-2, pp. 167-179, Mar. 15, 2002.
A. V. Khvostov et al., "ansa-Ytterbocene (III) choloride and borohydride with a short bridge and bulky substituents: synthesis and crystal structures of [meso-(CH3)2Si[3-(CH3)3SiC5H3]2Yb(m2-C1)]2 and meso-(CH3)2Si[3-(CH3)    3SiC5H3]2Yb [m2-H)3BH](THF)", Journal of Organometallic Chemistry, vol. 589, pp. 222-225, 1999.

* cited by examiner

*Primary Examiner* — Caixia Lu
(74) *Attorney, Agent, or Firm* — Cozen O'Connor

(57) ABSTRACT

Borohydride metallocene complex of lanthanide, preparation process, catalytic system incorporating it, copolymerization of olefins employing catalytic system and ethylene/butadiene copolymer, the butadiene units comprise 1,2-cyclohexane or 1,2- and 1,4-cyclohexane links. The complex corresponds to of formulae A and/or B:

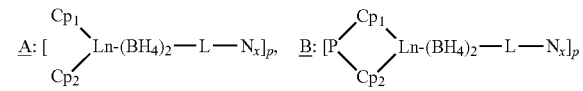

where, in A two ligands $Cp_1$ and $Cp_2$, each of a fluorenyl group, are connected to the lanthanide Ln, where, in B, a ligand molecule, composed of two fluorenyl groups $Cp_1$ and $Cp_2$ are connected via bridge P of formula $MR_1R_2$, is an element from group IVa, $R_1$ and $R_2$, which are identical or different, represent an alkyl group comprising from 1 to 20 carbon atoms, connected to lanthanide Ln, L is alkali metal, N is molecule of a complexing solvent, x is integral or non-integral number $\geq 0$ and p is integer $\geq 1$.

3 Claims, 5 Drawing Sheets

BOROHYDRIDE METALLOCENE COMPLEX OF A LANTHANIDE, CATALYTIC SYSTEM INCLUDING THE SAID COMPLEX, POLYMERISATION METHOD USING SAME AND ETHYLENE/BUTADIENE COPOLYMER OBTAINED USING SAID METHOD

CROSS REFERENCE TO RELATED APPLICATIONS

This application is a Divisional of U.S. patent application Ser. No. 12/084,808, filed Aug. 5, 2009, now U.S. Pat. No. 8,071,800, which claims priority from PCT Application No. PCT/EP2006/01453 filed on Oct. 31, 2006, and from an application filed in France on Nov. 9, 2005, No. 05/11393, respectively. The disclosure of which is incorporated herein by reference.

FIELD OF THE INVENTION

The present invention relates to a borohydride metallocene complex of a lanthanide, to its process of preparation, to a catalytic system incorporating this complex, to a process for the copolymerization of at least two olefinic monomers using this catalytic system and to a copolymer of ethylene and of butadiene obtained by this process, the units of which resulting from butadiene comprise 1,4-cyclohexane or 1,2-cyclohexane links.

BACKGROUND OF THE INVENTION

It is known to use catalytic systems based on halogenated metallocene complexes of lanthanides for copolymerizing ethylene and a conjugated diene.

The document EP-A-1 092 731 teaches the use, in producing copolymers of ethylene and a conjugated diene, of a catalytic system comprising:

on the one hand, an organometallic complex represented by one of the following generic formulae A or B:

where Ln represents a lanthanide metal having an atomic number which can range from 57 to 71, where X represents a halogen which can be chlorine, fluorine, bromine or iodine, where $Cp_1$ and $Cp_1$ each comprise a cyclopentadienyl or fluorenyl group which is substituted or unsubstituted and where P is a bridge corresponding to the formula $MR_1R_2$, where M is an element from Group IVa of the Periodic Table of the Elements and where $R_1$ and $R_2$ represent an alkyl group comprising from 1 to 20 carbon atoms, and on the other hand, a cocatalyst which is chosen from a group consisting of an alkylmagnesium, alkyllithium, alkylaluminium, and a Grignard reagent or which is composed of a mixture of these constituents.

The document Patent WO-A-2004/035639 on behalf of the Applicants teaches the use, in producing copolymers of ethylene and butadiene, of a catalytic system comprising:

(i) a lanthanide metallocene complex represented by one or other of the following formulae:

where Ln represents a lanthanide metal having an atomic number which can range from 57 to 71, where X represents a halogen which can be chlorine, fluorine, bromine or iodine, where, in the first formula, two identical or different ligand molecules $Cp_1$ and $Cp_2$, each composed of a fluorenyl group which is substituted or unsubstituted, are connected to the said metal Ln, and where, in the second formula, a ligand molecule composed of two identical or different fluorenyl groups $Cp_1$ and $Cp_2$ which are substituted or unsubstituted and which are connected to one another via a bridge P corresponding to the formula $MR_1R_2$, where M is an element from Group IVa of the Periodic Table of the Elements and where $R_1$ and $R_2$ represent an alkyl group comprising from 1 to 20 carbon atoms, is connected to the said metal Ln, and (ii) a cocatalyst belonging to the group consisting of an alkylmagnesium, an alkyllithium, an alkylaluminium, and a Grignard reagent or which is composed of a mixture of these constituents.

Other catalytic systems based on monocyclopentadienyl complexes of lanthanide borohydride type are known in particular in the literature for the homopolymerization of diolefins.

Mention may be made, for example, of the paper by D. Barbier-Baudry, O. Blacque, A. Hafid, A. Nyassi, H. Sitzmann and M. Visseaux, *European Journal of Inorganic Chemistry* 2000, 2333-2336, which mentions a complex of formula $(C_5H(iPr)_4)Ln(BH_4)_2(THF)$ including a monocyclopentadienyl ligand substituted by an isopropyl group (iPr), where THF is tetrahydrofuran, for the homopolymerization of isoprene or styrene after alkylation by a cocatalyst of organolithium type.

More recently, the paper by F. Bonnet, M. Visseaux, A. Pereira and D. Barbier-Baudry, *Macromolecules*, 2005, 38, 3162-3169, disclosed the use of a similar complex of formula $(C_5Me_4(nPr))Nd(BH_4)_2(THF)_2$ including a pentasubstituted monocyclopentadienyl ligand, where nPr is an n-propyl group, in the stereospecific 1,4-trans polymerization of isoprene after alkylation by a cocatalyst of dialkylmagnesium type.

It should be noted that these lanthanide borohydride monocyclopentadienyl complexes have not been used to date in the copolymerization of monoolefins and conjugated dienes.

The Chinese patent document 1 286 256 discloses, as polymerization catalysts for the synthesis of polymethacrylates, a borohydride metallocene complex of a lanthanide comprising a ligand molecule composed of a fluorenyl group corresponding to the following formula:

where:

$X_1$ represents an alkyl group having from 1 to 4 carbon atoms or a phenyl group, $X_2$ represents Cl, $BH_4$, H, an alkyl group having from 1 to 4 carbon atoms, $N[Si(CH_3)_3]_2$, $CH_2[Si(CH_3)_3]$ or tetrahydrofuran, $R_1$, $R_3$ and $R_4$ represent H or the $CH_3$ radical, $R_2$ represents H, $R_5$ and $R_6$ represent H, an alkyl group having from 1 to 4 carbon atoms or $Si(CH_3)_3$, $R_7$ represents Si, C, Ge or Sn, M represents a lanthanide, yttrium or scandium, L represents $Si(CH_3)_3$, $Li(THF)_4$, [crown ether Y] or [crown ether Y]-2,4-epoxyhexacycle, n represents 0 or 1 and m=1 or 2 (if m=2, n=0), Y is a monovalent metal.

Another recent research route has concerned borohydride metallocene complexes of lanthanides including a ligand based on two cyclopentadienyl groups. Mention may be made, for example, of the studies by S. M. Cendrowski-Guillaume et al., Organometallics, 2000, 19, 5654-5660, and Macromolecules, 2003, 36, 54-60, which have disclosed the use of such a metallocene complex, of formula $(C_5Me_5)_2Sm(BH_4)(THF)$, where Me is a methyl group and where Sm is samarium, for specifically catalysing the polymerization of ε-caprolactone by ring opening.

Mention may also be made of the studies by M. Visseaux et al., Journal of Organometallic Chemistry, 691 (2006), pages 86-92, which have disclosed that the metallocene $Cp^*_2Nd(BH_4)(THF)$, when it is used in combination with butylethylmagnesium, even in the presence of a large excess of THF, constitutes a very active catalyst for ethylene and, in the presence of a stoichiometric amount of butylethylmagnesium, makes possible the stereospecific 1,4-trans polymerization of isoprene.

SUMMARY OF THE INVENTION

One object of the present invention is to achieve the copolymerization of olefins and conjugated dienes using borohydrate metallocene complexes of lanthanides.

This and other objects are attained in accordance with one aspect of the present invention directed to a borohydride metallocene complex of a lanthanide corresponding to one or other of the following two formulae A and B:

where Ln is a lanthanide having an atomic number of between 57 and 71 inclusive, where, in the formula A, two identical or different ligand molecules $Cp_1$ and $Cp_2$, each composed of a fluorenyl group which is substituted or unsubstituted, are connected to Ln, where, in the formula B, a ligand molecule composed of two identical or different fluorenyl groups $Cp_1$ and $Cp_2$ which are substituted or unsubstituted and which are connected to one another via a bridge P corresponding to the formula $MR_1R_2$, where M is an element from Group IVa of the Periodic Table of the Elements and where $R_1$ and $R_2$, which are identical or different, represent an alkyl group comprising from 1 to 20 carbon atoms, is connected to Ln, where L represents an alkali metal chosen from the group consisting of lithium, sodium and potassium, where N represents a molecule of a complexing solvent, such as an ether, where x is an integral or non-integral number which is greater than 0 and where p is an integer which is equal to 1 or 2, can be used for the copolymerization of olefins and in particular for the copolymerization of monoolefins and conjugated dienes and more specifically still for producing, with a high catalytic activity, copolymers of ethylene and butadiene where the units resulting from the butadiene comprise 1,2-cyclohexane links.

It should be noted that this borohydride metallocene complex of a lanthanide according to the invention is, to the knowledge of the Applicants, the very first to date which makes possible the synthesis of a copolymer of at least one olefin and at least one conjugated diene comprising 1,2-cyclohexane links, when it is used in combination with an alkylation cocatalyst chosen from the group consisting of an alkylmagnesium, an alkyllithium, a Grignard reagent and a mixture of an alkyllithium and of an alkylaluminium.

As emerges from the above formulae A and B, it should be noted that this lanthanide metallocene complex according to the invention (also known as "lanthanidocene" by a person skilled in the art) specifically includes, on the one hand, two fluorenyl and borohydride groups connected to the lanthanide and, on the other hand, the alkali metal L, preferably lithium, associated with the molecule of complexing solvent N, which is preferably composed of tetrahydrofuran (THF).

Preferably, $Cp_1$ and $Cp_2$ are each composed of the same unsubstituted fluorenyl group which corresponds to the formula $C_{13}H_9$ or $C_{13}H_8$ for the formula A or B respectively.

Also preferably, these formulae A and B are such that x is equal to 1 and p is equal to 2, the complex according to the invention then being a dimer in both cases.

According to a particularly advantageous embodiment of the invention, the said complex corresponds specifically to the formula B, being in this case of type bridged via the bridge of formula $MR_1R_2$ in which the element M is preferably silicon and $R_1$ and $R_2$ are advantageously a methyl group.

More advantageously still, the said complex according to the invention corresponds to either of the formulae:

where Flu represents an unsubstituted fluorenyl group of formula $C_{13}H_8$ in the complex B' or a fluorenyl group substituted by an alkyl group comprising from 1 to 20 carbon atoms in the group B", where Me represents a methyl group, Si is silicon, Nd is neodymium, Li is lithium, $Et_2O$ is an ether and x is an integer ranging from 0 to 3.

According to another advantageous characteristic of the invention, the said complex can be isolated in the form of single crystals, which makes it possible in particular to analyse it by the X-ray diffraction technique (see appended Annex 1) in order to obtain crystallographic data. More specifically, the Applicants have been able to establish that these single crystals of the complex B' according to the invention are arranged according to a monoclinic lattice system.

The said complex according to the invention is advantageously obtained by a preparation process comprising the reaction of a ligand salt of formula $P-Cp_1Cp_2-L_2$ and of a lanthanide Ln tris(borohydride) dissolved in the said complexing solvent and of formula $Ln(BH_4)_3N_3$.

Preferably, in connection with the formula B' according to the invention, the said ligand salt corresponds to the formula $Me_2SiFlu_2-Li_2$ and the said lanthanide tris(borohydride) corresponds to the formula $Nd(BH_4)_3(THF)_3$.

According to one embodiment of the invention, this preparation process comprises running, at ambient temperature, the said ligand salt, dissolved in another solvent, such as diethyl ether, onto the said solution of lanthanide tris(borohydride), in the form dissolved in this other solvent, stirring the solution at ambient temperature, filtering the stirred solution, concentrating the filtrate and/or drying the complex, and optionally adding a poor solvent to the concentrate in order to precipitate the complex.

A catalytic system according to the invention comprises, on the one hand, the said borohydride metallocene complex of a lanthanide as defined above and, on the other hand, the said cocatalyst chosen from the group consisting of an alkylmagnesium, an alkyllithium, a Grignard reagent and a mixture of an alkyllithium and of an alkylaluminium.

Advantageously, the said cocatalyst is butyloctylmagnesium.

As indicated above, this catalytic system according to the invention advantageously makes it possible to copolymerize several olefins, such as monoolefins and diolefins, which was not made possible by any catalytic system of the prior art based on a metallocene complex of lanthanide borohydride type.

It should also be noted that the said lanthanide borohydride metallocene complex confers, on the catalytic system according to the invention, a catalytic activity for the copolymerization of a monoolefin, such as ethylene, and a conjugated diene, such as butadiene, which is even higher than that provided by the halogenated metallocene complex of the abovementioned document WO-A-2004/035639 for the same copolymerization reaction.

A process for the copolymerization according to the invention of at least two olefinic monomers, such as a monoolefin and/or a diolefin, comprises a reaction of the said catalytic system in the presence of the said monomers and this reaction is preferably carried out in suspension or in solution in a hydrocarbon solvent, such as toluene, and at a temperature of between −20° C. and 120° C.

This reaction can be carried out under a variable pressure, preferably ranging from 1 bar to 50 bar, and, also preferably, at a temperature preferably of between 20° C. and 90° C.

The copolymerization process preferably comprises:
(i) the preliminary preparation of the said catalytic system outside the polymerization medium by reacting the said complex with the said cocatalyst, then
(ii) the reaction of the catalytic system obtained in (i) in the presence of the monomers to be polymerized.

In an alternative form, it should be noted, however, that the catalytic system might be formed in situ in the polymerization medium.

According to a particularly advantageous embodiment of the invention, this process comprises the copolymerization of ethylene and butadiene in order to obtain an ethylene/butadiene copolymer in which:
the molar level of units resulting from butadiene is advantageously greater than 10% and more advantageously still equal to or greater than 25%, and in which
the units resulting from butadiene comprise cyclic links in the form of 1,2-cyclohexane, in addition to the usual trans-1,4 and 1,2 (vinyl) links.

Advantageously, the molar level of the 1,2-cyclohexane links in the units of the said copolymer which result from butadiene is equal to or greater than 20% and more advantageously still equal to or greater than 25%. It should be noted that, in some cases, this level of 1,2-cyclohexane links can even be greater than 35%.

According to another characteristic of the invention, use is made of a cocatalyst/complex molar ratio of less than or equal to 10 and advantageously of less than or equal to 5, in order to obtain a number-average molecular weight Mn of the said copolymer which is equal to or greater than 50,000 g/mol.

More advantageously still, this cocatalyst/complex molar ratio is chosen to be less than or equal to 2 and the copolymerization is carried out under a pressure equal to or greater than 8 bar, for example equal to 10 bar, in order to obtain a number-average molecular weight Mn of the said copolymer which is equal to or greater than 200,000 g/mol.

A copolymer of ethylene and butadiene according to the invention which is capable of being obtained by the copolymerization process defined above advantageously exhibits both:
a) a molar level of units resulting from butadiene which is equal to or greater than 25%, and
b) a molar level of 1,2-cyclohexane links in the said units resulting from butadiene which is equal to or greater than 25%.

According to another characteristic of the invention, this copolymer of ethylene and butadiene exhibits, in addition to the two abovementioned characteristics a) and b), a number-average molecular weight Mn equal to or greater than 30,000 g/mol.

Advantageously, these copolymers according to the invention furthermore exhibit a polydispersity index PI which is less than 3.5 and more advantageously still less than or equal to 2.5. Following the example of the molecular weights Mn, the polydispersity indices PI were determined in the present description by steric exclusion chromatography (see the appended Annex 2).

The copolymers according to the invention preferably exhibit a glass transition temperature Tg which is less than −10° C. More specifically, these copolymers can, for example, exhibit a temperature Tg of between −20° C. and −50° C. This temperature Tg is measured in the present description by the Differential Scanning calorimetry (DSC) technique. More specifically, these thermal analyses were carried out on a "Setaram 131" calorimeter. The samples were subjected to two rises in temperature from −100° C. to 100° C. at the rate of $10°$ C.·min$^{-1}$. The data of the second rise in temperature were used to determine the thermal properties of the polymers.

DETAILED DESCRIPTION OF THE DRAWINGS

For all the following examples, the procedure was carried out under argon and the solvents used were dried beforehand by a reaction with sodium, followed by distillation, or else over a 3 Å molecular sieve while flushing with argon.

All the metallocene complexes synthesised below were analysed by $^1$H NMR in $d_8$-THF at a temperature of 22° C. using a "Bruker DRX 300" spectrometer at a frequency of 300 MHz and additionally, for the borohydride complex according to the invention, by the X-ray diffraction technique described in the appended Annex 1.

The microstructure of each copolymer obtained in these examples was determined by $^1$H NMR and $^{13}$C NMR techniques. To this end, use is made of a "Bruker DRX 400" spectrometer at frequencies of 400 MHz for the $^1$H NMR technique and of 100.6 MHz for the $^{13}$C NMR technique. The spectra were acquired using a 5 mm "QNP" probe at a temperature of 363 K. A tetrachloroethylene/perdeuterobenzene mixture (ratio by volume 2:1) was used as solvent.

1) Synthesis of a Complex 1 of Lanthanide Borohydride Metallocene Type According to the Invention of Formula [Me$_2$SiFlu$_2$Nd(BH$_4$)$_2$Li(THF)]$_2$ a) A salt of Me$_2$SiFlu$_2$Li$_2$ (Me and Flu respectively being a methyl group and an unsubstituted fluorenyl group) was synthesised as described in the document of Patent EP-A-1 092 731.

To this end, in a first step, a compound of formula Me$_2$Si(C$_{13}$H$_9$)$_2$ was synthesised. In order to do this, 18 mmol of C$_{13}$H$_1$ and 18 mmol of sodium hydride were stirred at reflux in THF overnight. 8.1 mmol of Cl$_2$SiMe$_2$ were subsequently added to this mixture and then the solution obtained was stirred at ambient temperature for 3 hours. A portion of the THF was subsequently evaporated and then heptane was added. The organic phase obtained was hydrolysed and was extracted several times with a saturated aqueous NH$_4$Cl solution. The solvent was then evaporated and, after drying the extract under vacuum at 60° C., the said compound of formula Me$_2$Si(C$_{13}$H$_9$)$_2$ was finally recovered.

4.4 mmol of this compound of formula Me$_2$Si(C$_{13}$H$_9$)$_2$ and 13 mmol of BuLi were subsequently stirred in toluene at ambient temperature overnight and then at 50° C. for 3 hours. The precipitate composed of a corresponding salt of formula Me$_2$SiFlu$_2$Li$_2$ was obtained and was washed with heptane and then dried under vacuum.

b) Furthermore, the neodymium borohydride of formula Nd(BH$_4$)$_3$(THF)$_3$ was synthesised as described in the paper by S. M. Cendrowski-Guillaume, G. Le Gland, M. Nierlich and M. Ephritikhine, *Organometallics*, 2000, 19, 5654-5660.

c) The complex 1 according to the invention was then synthesised in the following way.

515 mg (1.3 mmol) of the salt Me$_2$SiFlu$_2$Li$_2$, dissolved in 75 ml of diethyl ether, were run at ambient temperature onto a solution comprising 521 mg of Nd(BH$_4$)$_3$(THF)$_3$ (1.3 mmol) dissolved in 75 ml of diethyl ether.

The solution obtained was stirred at ambient temperature for 12 hours and filtered, and then the filtrate obtained was concentrated down to a total volume of 125 ml. 200 ml of pentane was subsequently run in with stirring. After the appearance of a diffuse cloudiness, stirring was halted.

Dark red crystals (360 mg, 0.56 mmol) formed after standing for 12 hours.

Figure 1:
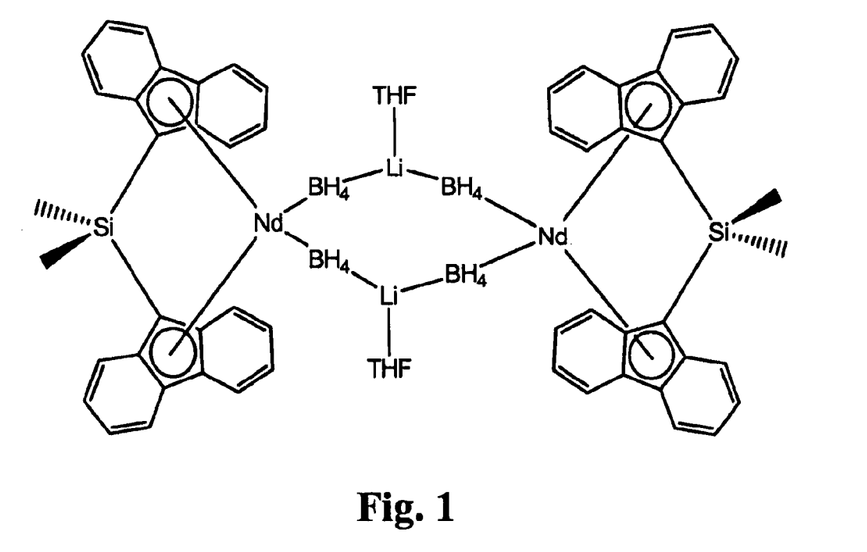
FIG. 1 illustrates the expanded chemical formula of a borohydride metallocene complex of a lanthanide according to an embodiment of the invention.

Thus, this reaction, at ambient temperature, resulted in the neodymium complex 1 according to the invention of molecular formula [Me$_2$SiFlu$_2$Nd(BH$_4$)$_2$Li(THF)]$_2$, the expanded formula being illustrated in FIG. 1. This complex 1 was isolated in the form of single crystals with a yield of 45%.

Figure 3:
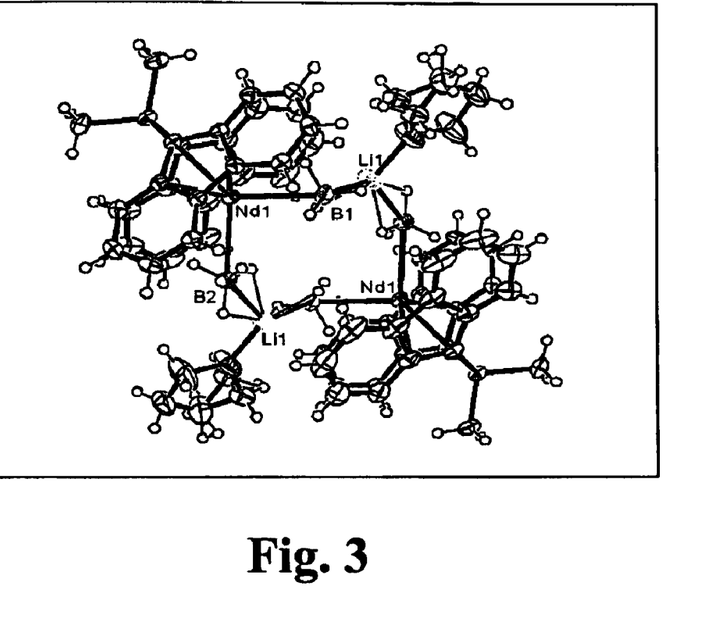
Figure 4:
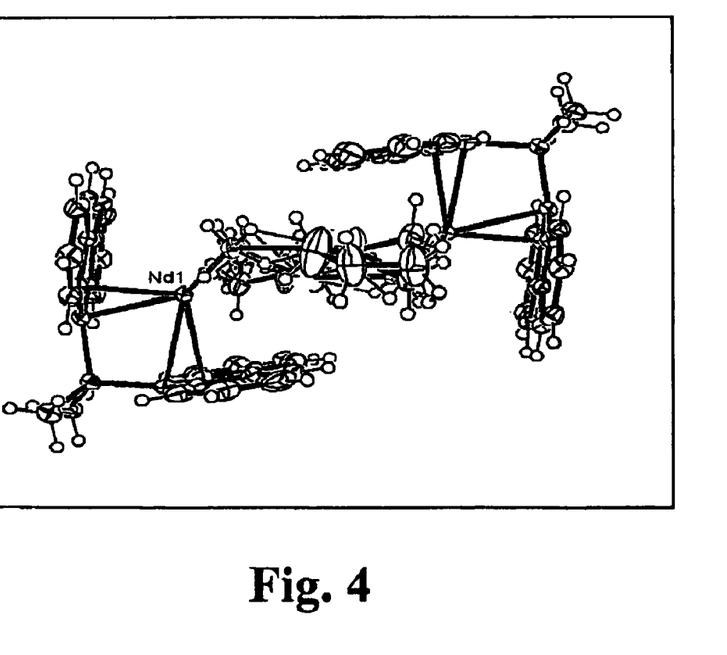

These single crystals of the complex 1 were characterized by X-ray diffraction and by $^1$H NMR, as illustrated in FIGS. 3 and 4 and in the appended Annex 1, which shows in particular that these single crystals are arranged according to the monoclinic lattice system.

As emerges from the characterization by X-ray diffraction (FIG. 3 and FIG. 4), the complex 1 according to the invention of empirical formula [Me$_2$SiFlu$_2$Nd(BH$_4$)$_2$Li(THF)]$_2$ exists in the form of a dimer.

Figure 5:
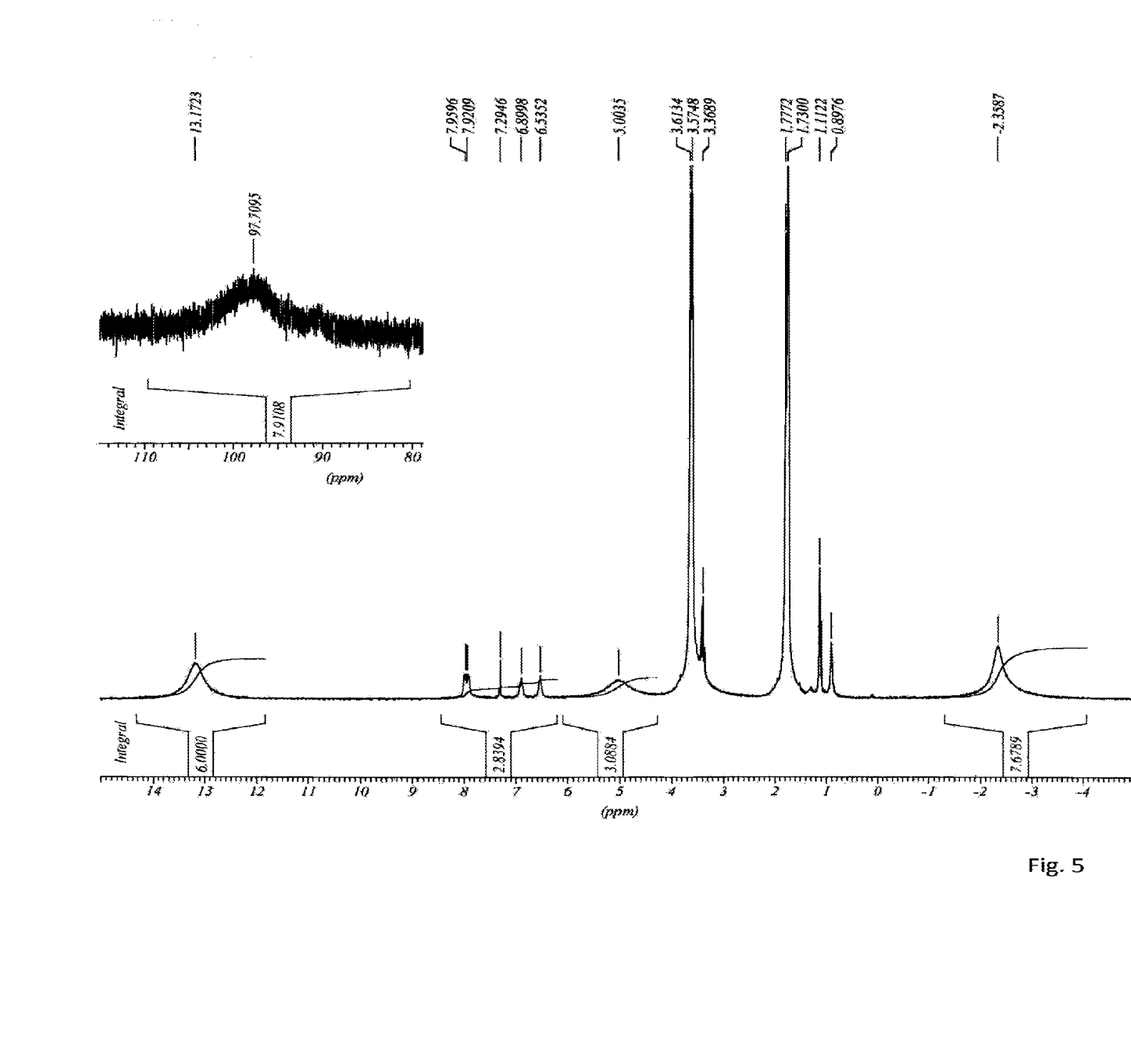
FIG. 5 is a $^1$H NMR spectrum relating to the complex according to an embodiment of the invention of FIG. 1 where only the high fields are represented (the signal relating to the BH$_4$ groups is not represented and appears at approximately 100 ppm)

The molar mass $M_1$ of the dimer is equal to 1279.10 g·mol$^{-1}$. The $^1$H NMR analysis confirms the structure of this complex 1 and the following assignment has been proposed for this complex 1:

($d_8$-THF, 22° C.): 97.5 ppm, 8H, BH$_4$; 13.15 ppm, 6H, Si(CH$_3$)$_2$; 5 ppm, 4H, Flu; −2.35 ppm, 2*4H, Flu.

2) Synthesis of a "Control" Complex 2 of the Prior State of the Art of Lanthanide Halogenated Metallocene Type of Formula [Me$_2$SiFlu$_2$]NdCl 1090 mg (2.8 mmol) of Me$_2$SiFlu$_2$Li$_2$, dissolved in 50 ml of THF, were run at ambient temperature onto a solution comprising 620 mg (2.5 mmol) of NdCl$_3$ in 100 ml of THF (the NdCl$_3$ suspension was heated at reflux beforehand for 12 hours). The mixture was brought to reflux for 12 hours and then the solvent was evaporated. The product was extracted with toluene and a salt was removed by filtration. 1390 mg (2.4 mmol) of crude complex were obtained after evaporation of the filtrate, chloro(µ-dimethylsilyl)bis($\eta^5$-fluorenyl) neodymium of formula [Me$_2$SiFlu$_2$]NdCl and of molar mass M=566.27 g/mol.

This reaction required bringing the reaction medium to reflux and resulted in the complex 2 isolated in the form of a crude product. The X-ray diffraction analysis of this complex 2 was not possible as single crystals could not be obtained for this complex 2. Due to the paramagnetism of neodymium, no signal relating to the complex 2 could be observed by $^1$H NMR, whether in $d_8$-THF or in $d_5$-pyridine.

3) Low-Pressure Copolymerization Tests (Starting Pressure=4 bar)

Each of these two complexes 1 and 2 was used in association with butyloctylmagnesium (abbreviated to "BOMAG") as alkylating cocatalyst for the copolymerization of ethylene and butadiene. Each catalytic system 1 and 2 (respectively according to the invention and "control") was prepared by carrying out a prior activation of the corresponding complex 1 or 2 by the cocatalyst "BOMAG" according to an Mg cocatalyst/Nd complex molar ratio varying from 1.9 to 10.4, the activation time being;

15 min for the tests 3-1, 3-2, 3-3 and 3-6, 12 h for the test 3-4, and 1 h for the test 3-5.

The polymerizations took place in a 250 ml glass reactor in 200 ml of toluene at a temperature of 80° C. and a starting pressure of 4 bar. The monomers were introduced into the medium in the form of a gas mixture comprising 30% of butadiene.

After a reaction time t (min), the copolymerization is halted by cooling and degassing the reactor and then the copolymer is obtained by precipitation from methanol. After drying, a weight w (g) of copolymer is obtained.

The results of the various tests are listed in Tables 1 to 3 below.

TABLE 1

Polymerization conditions

| Tests | Complex | Com-plex in mg | [Nd] in μmol·l$^{-1}$ | [Mg] in μmol·l$^{-1}$ | [Mg]/[Nd] | Weight of co-polymer w in g | Time in min |
|---|---|---|---|---|---|---|---|
| 3-1 | 1 | 10.0 | 78 | 266 | 3.4 | 1.10 | 60 |
| 3-2 | 1 | 26.9 | 210 | 1064 | 5.1 | 11.00 | 180 |
| 3-3 | 1 | 13.1 | 102 | 1064 | 10.4 | 7.5 | 180 |
| 3-4 | 1 | 13.0 | 102 | 1064 | 10.4 | 7.8 | 180 |
| 3-5 | 1 | 27.7 | 217 | 418 | 1.9 | 12.6 | 180 |
| 3-6 | 2 (control) | 33.0 | 194 | 388 | 2 | 8.50 | 240 |

TABLE 2

Activities of the complexes and macrostructure of the copolymers

| Tests | Activity in g·mol$^{-1}$·h$^{-1}$ | Activity in g·g$^{-1}$·h$^{-1}$ | Mn in g·mol$^{-1}$ | PI | Tg in °C. |
|---|---|---|---|---|---|
| 3-1 | 70 500 | 110 | 50 800 | 2.59 | −40.2 |
| 3-2 | 87 300 | 136 | 46 150 | 1.60 | −36.0 |
| 3-3 | 122 550 | 191 | 33 300 | 1.68 | −35.3 |
| 3-4 | 127 450 | 200 | 37 400 | 1.69 | −37.1 |
| 3-5 | 96 800 | 152 | 74 850 | 1.54 | −33.0 |
| 3-6 (control) | 36 500 | 64 | 110 000 | 2.30 | −37.0 | where the columns expressed in g·mol$^{-1}$·h$^{-1}$ and in g·g$^{-1}$·h$^{-1}$ indicate the number of grams of copolymer obtained per mole (respectively per gram) of complex and per hour, thus constituting indicators of the catalytic activity of the complexes 1 and 2.

TABLE 3

$^{13}$C NMR characterization of the microstructure of the copolymers

| Test | Molar % butadiene units | Molar % 1,4-trans links | Molar % 1,2 links | Molar % 1,2-cyclohexane links |
|---|---|---|---|---|
| 3-2 | 26.7 | 31.8 | 35.2 | 33.0 |
| 3-3 | 28.0 | 32.3 | 38.9 | 28.8 |
| 3-4 | 28.4 | 32.1 | 38.8 | 29.1 |
| 3-5 | 25.3 | 31.9 | 31.9 | 36.1 |
| 3-6 (control) | 19.3 | 28.9 | 27.9 | 43.2 |

Figure 2:
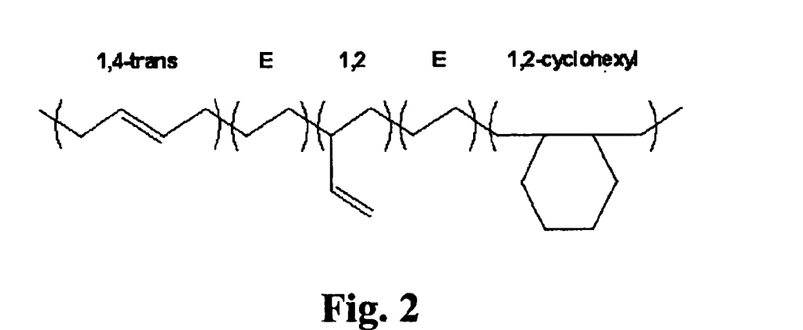
FIG. 2 illustrates the various links characterizing the insertion of the units resulting from butadiene into a copolymer of ethylene and butadiene prepared according to an embodiment of the invention by means of the complex of FIG. 1, FIGS. 3 and 4 each illustrate the structure of the single crystals observed by X-ray diffraction which characterizes the complex according to an embodiment of the invention of FIG. 1.

FIG. 2 is a schematic illustration of the various links observed for the insertion of butadiene units in the ethylene/butadiene copolymers thus prepared.

In the light of Table 2, it is apparent that the lanthanide borohydride metallocene complex 1 according to the invention, once alkylated by the cocatalyst, exhibits a much greater catalytic activity in g·g$^{-1}$·h$^{-1}$ than that of the "control" complex 2 which is at least substantially doubled, indeed even tripled (cf. tests 3-3 and 3-4), in comparison with that of this "control" complex of lanthanide halogenated metallocene type (cf. test 3-6).

In the light of Table 3, it is apparent that this complex 1 according to the invention makes it possible to obtain ethylene/butadiene copolymers in which the units resulting from butadiene are present according to a molar level of greater than 25% and always comprise 1,2-cyclohexane links, units resulting from butadiene, according to a relatively high molar level which is equal to or greater than 25%, indeed even 30%.

Thus, the test 3-4 according to the invention results in the production of a copolymer comprising 28.4% of units resulting from butadiene, including 29.1% of 1,2-cyclohexane links, with a catalytic activity of 200 g·g$^{-1}$·h$^{-1}$ for the complex 1 used, against only 64 g·g$^{-1}$·h$^{-1}$ for the "control" complex 2.

In addition, the test 3-5 according to the invention shows that it is possible to obtain a relatively high number-average molar mass Mn for the ethylene/butadiene copolymer (greater than 70 000 g/mol) by choosing a cocatalyst/complex molar ratio of less than 2.

4) High-Pressure Copolymerization Tests (Starting Pressure=10 bar)

Each of the two complexes 1 and 2 was used in association with "BOMAG" as alkylation cocatalyst and according to the same Mg cocatalyst/Nd complex molar ratio equal to 2 for the copolymerization of ethylene and butadiene. Each catalytic system 1 and 2 (respectively according to the invention and "control") was prepared by carrying out a prior activation of the corresponding complex 1 or 2 by the cocatalyst "BOMAG" for a time of 15 min.

The polymerizations took place in a 1 liter metal reactor made of stainless steel, in 600 ml of toluene at 80° C. and at a starting pressure of 10 bar. The butadiene and ethylene monomers (respectively abbreviated to "Bd" and "E") were introduced into the medium while varying the fraction of butadiene in the feed gas mixture.

The results of the various tests are listed in Tables 4 to 6 below.

TABLE 4

Polymerization conditions

| Tests | Complex | Com-plex in mg | [Nd] in μmol·l$^{-1}$ | Bd in g | E in g | % Bd Feed | Weight of co-polymer w in g | Polym. time |
|---|---|---|---|---|---|---|---|---|
| 4-1 | 1 | 33.3 | 87 | 8.1 | 24.95 | 14.4 | 25.6 | 1h 00 |
| 4-2 | 1 | 34.0 | 88 | 22.6 | 24.35 | 32.5 | 31.7 | 2h 45 |
| 4-3 | 2 (control) | 22.0 | 65 | 8 | ≈25 | ≈14 | 5.9 | 3h 00 |
| 4-4 | 2 (control) | 47.2 | 138 | 18 | ≈25 | ≈30 | 15.8 | 2h 20 |

TABLE 5

Activities of the complexes and macrostructure of the copolymers

| Tests | Activity in g·mol$^{-1}$·h$^{-1}$ | Activity in g·g$^{-1}$·h$^{-1}$ | Mn in g·mol$^{-1}$ | PI | Tg in °C. |
|---|---|---|---|---|---|
| 4-1 | 492 300 | 769 | 297 000 | 3.16 | −36.0 |
| 4-2 | 217 500 | 339 | 281 000 | 1.92 | −45.6 |
| 4-3 (control) | 50 400 | 89 | 378 600 | 2.8 | −43.2 |
| 4-4 (control) | 81 600 | 143 | 70 700 | 2.0 | −45.7 | where the columns expressed in g·mol$^{-1}$·h$^{-1}$ and in g·g$^{-1}$·h$^{-1}$ also indicate the number of grams of copolymer obtained per mole (respectively per gram) of complex and per hour, thus constituting indicators of the catalytic activity of the complexes 1 and 2.

TABLE 6

$^1$H NMR characterization of the microstructure of the copolymers

| Tests | Molar % Bd in feed | Molar % Bd in copolymer | Molar % 1,4-trans links | Molar % 1,2 links | Molar % 1,2-cyclohexane links |
|---|---|---|---|---|---|
| 4-1 | 14.4 | 12.9 | 25.3 | 39.6 | 35.1 |
| 4-2 | 32.5 | 30.8 | 29.6 | 50.3 | 20.2 |
| 4-3 (control) | ≈14 | 20 | 26.7 | 44.5 | 28.8 |
| 4-4 (control) | ≈30 | 30.4 | 27.8 | 53.5 | 18.7 |

In light of Table 5, it is apparent that the lanthanide borohydride metallocene complex 1 according to the invention, once alkylated by the cocatalyst, exhibits a much greater catalytic activity in g·g$^{-1}$·h$^{-1}$ than that of the "control" complex 2 which is more than doubled, indeed even more than quadrupled (cf. tests 4-1 and 4-2), in comparison with that of this "control" complex of lanthanide halogenated metallocene type (cf. tests 4-3 and 4-4).

In light of Table 6, it is apparent that this complex 1 according to the invention makes it possible to obtain ethylene/butadiene copolymers in which the units resulting from butadiene are present according to a molar level of greater than 10%, indeed even 30%, and always comprise 1,2-cyclohexane links according to a relatively high molar level which is greater than 20%, indeed even 30%.

Thus, the test 4-2 according to the invention results in the production of a copolymer comprising 30.8% of the units resulting from butadiene, including 20.2% of 1,2-cyclohexane links, with a catalytic activity of 339 g·g$^{-1}$·h$^{-1}$ for the complex 1 used, against only 143 g·g$^{-1}$·h$^{-1}$ for the "control" complex 2 tested in the test 4-4, carried out under polymerization conditions similar to those of the test 4-2, as a result of a butadiene feed of approximately 30% (cf. Table 4).

It should also be noted that these high-pressure (10 bar) polymerizations, which are associated with a reduced Mg cocatalyst/Nd complex molar ratio (equal to 2), allow the complex 1 of the invention to confer, on the copolymer obtained in the test 4-2, a much greater molar mass Mn (greater than 281 000 g/mol) than that provided by the "control" complex 2 (70 700 g/mol) under the similar conditions of the test 4-4.

In conclusion, the lanthanide borohydride metallocene complex 1 according to the invention makes it possible to prepare copolymers of ethylene and butadiene exhibiting 1,2-cyclohexane units with very high catalytic activities which are the highest known to date to the knowledge of the Applicants.

5) Low-Pressure Homopolymerization Test (Starting Pressure=4 bar)

Use was made of the complex 1 in association with butyloctylmagnesium (abbreviated to "BOMAG") as alkylating cocatalyst for the polymerization of ethylene. The catalytic system according to the invention was prepared by carrying out a prior activation of the complex 1 by the cocatalyst "BOMAG" according to an Mg cocatalyst/Nd complex molar ratio of 10.4, the activation time being 15 min.

The polymerization took place in a 250 ml glass reactor, in 200 ml of toluene at a temperature of 80° C. and at a pressure of 4 bar.

After reacting for 25 minutes, the polymerization is halted by cooling and degassing the reactor and then the polymer is obtained by precipitating from methanol. After drying, 7.1 g of polyethylene, having an Mn=7700 g·mol$^{-1}$ and a polydispersity index PI=1.98, are obtained.

| Test | Complex | Complex in mg | [Nd] μmol·l$^{-1}$ | [Mg] in μmol·l$^{-1}$ | [Mg]/[Nd] | Weight of homopolymer w in g | Time in min |
|---|---|---|---|---|---|---|---|
| 5-1 | 1 | 13.1 | 102 | 1065 | 10.4 | 7.1 | 25 |

The lanthanide borohydride metallocene complex 1 according to the invention, once alkylated by the cocatalyst, exhibits a catalytic activity in g·mol$^{-1}$·h$^{-1}$ of 831 900.

6) Synthesis of a Complex 3 of Lanthanide Borohydride Metallocene Type According to the Invention of Formula Me$_2$SiFlu'$_2$Nd(BH$_4$)$_2$Li(ether)$_3$ (Flu'=2,7-$^t$Bu$_2$C$_{13}$H$_6$)

a) A salt of formula [Me$_2$SiFlu'$_2$]Li$_2$(THF)$_2$ was synthesised (Me and Flu' respectively being a methyl group and the 2,7-di(tert-butylfluorenyl ligand).

To this end, in a first step, a compound of formula [2,7-$^t$Bu$_2$C$_{13}$H$_7$][Li] was synthesised. 17.8 ml of a BuLi solution (1.6M, 28.4 mmol) were run onto a solution of 2,7-$^t$Bu$_2$C$_{13}$H$_8$ (7.54 g, 27.1 mmol) in toluene (50 ml). The mixture was stirred at ambient temperature for 15 hours and then brought to 60° C. for 2 hours. The salt which precipitates is recovered by filtration. [2,7-$^t$Bu$_2$C$_{13}$H$_7$][Li] is subsequently washed with heptane and then dried under vacuum (5.88 g, 76%).

3.64 g of [2,7-$^t$Bu$_2$C$_{13}$H$_7$][Li] (12.8 mmol) are dissolved in THF (150 ml). The solution is cooled to −50° C. and then SiMe$_2$Cl$_2$ is added (6.4 mmol). The mixture is brought back to ambient temperature and is then stirred for 15 hours. The THF is evaporated and then the product is extracted with 50 ml of toluene. The solvent is evaporated to give a beige solid of formula Me$_2$Si(2,7-$^t$Bu$_2$C$_{13}$H$_7$)$_2$. The compound Me$_2$Si(2,7-$^t$Bu$_2$C$_{13}$H$_7$)$_2$ is subsequently dissolved in 50 ml of THF. The solution is cooled to 0° C. and then 8.0 ml of a BuLi solution (1.6M, 12.8 mmol) are added. The mixture is brought back to ambient temperature and is then stirred for 15 hours. The THF is evaporated and the product is washed with cold heptane. 4.8 g of dilithium salt [Me$_2$Si(2,7-$^t$Bu$_2$C$_{13}$H$_6$)$_2$]Li$_2$(THF)$_2$ are obtained (97%).

The product was characterized by proton NMR and its molecular formula is: [Me$_2$Si(2,7-$^t$Bu$_2$C$_{13}$H$_6$)$_2$]Li$_2$(THF)$_2$ (MW=769.10 g·mol$^{-1}$).

The assignments are:

$^1$H NMR (d$_8$-THF, 22° C.): 0.96 ppm (s, 6H, SiMe$_2$); 1.39 ppm (s, 36H, t-Bu); 1.78 and 3.62 ppm (m, 2*8H, 2*THF); 6.65 ppm (d, J=8 Hz, 4H, FluH); 7.78 ppm (d, J=8 Hz, 4H, FluH); 8.02 ppm (s, 4H, FluH).

b) Furthermore, the neodymium borohydride of formula Nd(BH$_4$)$_3$(THF)$_3$ was synthesised as described in the paper by S. M. Cendrowski-Guillaume, G. Le Gland, M. Nierlich and M. Ephritikhine, *Organometallics,* 2000, 19, 5654-5660.

c) The compound 3 according to the invention was then synthesised in the following way:

The salt [Me$_2$Si(2,7-$^t$Bu$_2$C$_{13}$H$_6$)$_2$]Li$_2$(THF)$_2$ (6.4 mmol), dissolved in 75 ml of THF, was run at ambient temperature onto a solution comprising 2.59 g (6.4 mmol) of Nd(BH$_4$)$_3$(THF)$_3$ dissolved in 75 ml of THF. The mixture is kept stirred for 15 hours and then the solvent is evaporated. A residue which is red-brown in colour is obtained. Diethyl ether (175 ml) is subsequently added. The solution obtained is filtered and then the filtrate is concentrated down to a total volume of approximately 75 ml (appearance of cloudiness). 75 ml of pentane are then added with stirring. Stirring is halted and the solution is left standing. Crystals are formed, along with an oil. The supernatant is removed and lengthy drying is carried out under vacuum. A solid residue mixed with crystals is obtained (2.45 g).

Figure 6:
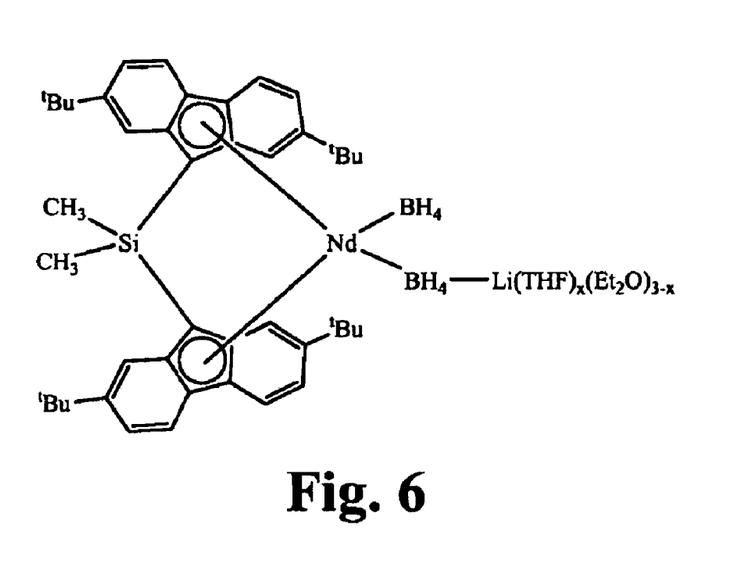
FIG. 6 illustrates the expanded chemical formula of another lanthanide borohydride metallocene complex according to an embodiment of the invention, FIGS. 7 and 8 each illustrate the structure of the single crystals observed by X-ray diffraction which characterizes the complex according to an embodiment of the invention of FIG. 6 (the carbon atoms of the ethers have been omitted from the representation for greater clarity).

Thus, this reaction at ambient temperature resulted in the neodymium complex 3 according to the invention of molecular formula [Me$_2$Si(Flu')$_2$Nd(BH$_4$)$_2$Li(ether)$_3$], the expanded formula being illustrated in FIG. 6.

Figure 7:
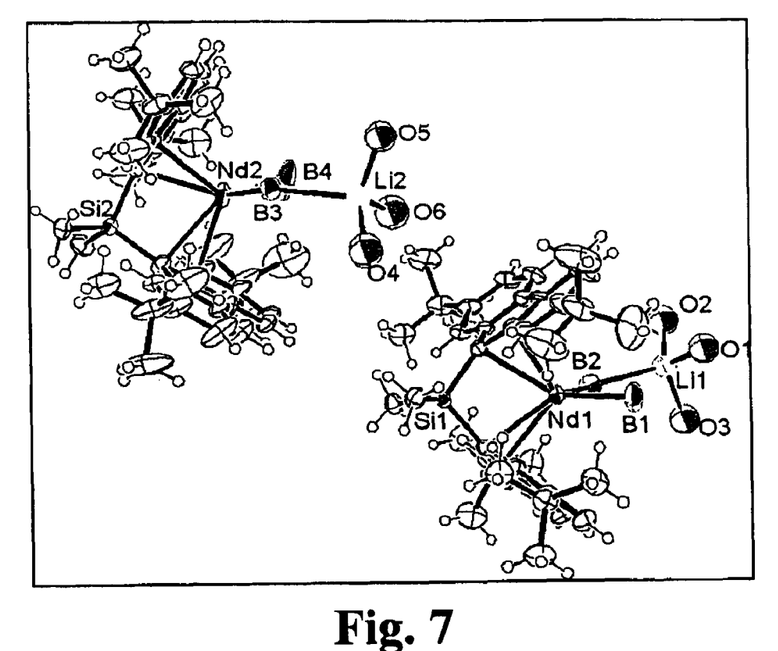
Figure 8:
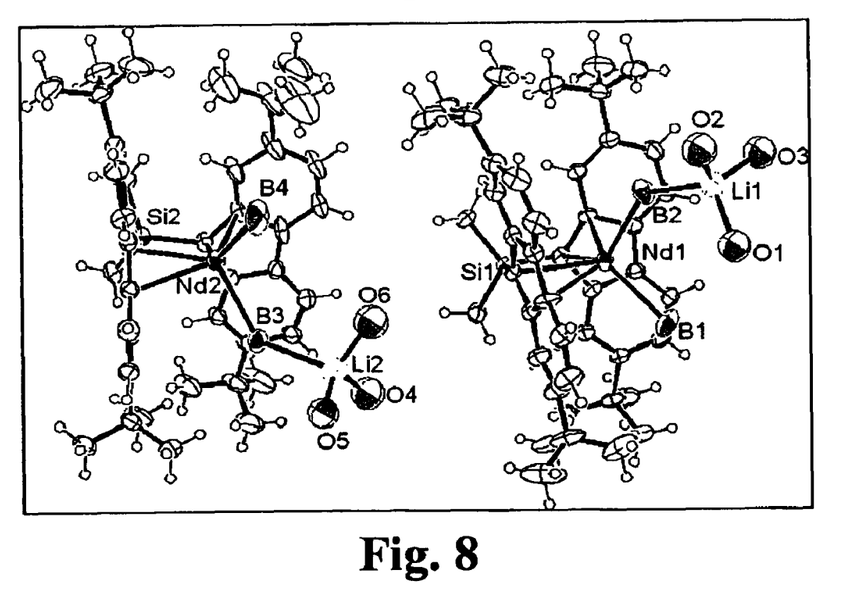

The single crystals of the complex 3 were characterized by X-ray diffraction, as illustrated in FIGS. 7 and 8, which show in particular that the crystals are arranged according to the triclinic lattice system. The complex 3 according to the invention furthermore exists in the monomeric form and the unit cell comprises two crystallographically independent complexes.

Its molar mass $M_3$ is between 1008 and 1012 g·mol$^{-1}$ depending on whether the ether molecules of the structure are THF, diethyl ether or a mixture of the two.

7) Low-Pressure Copolymerization Tests

Use was made of the complex 3 in association with butyloctylmagnesium (abbreviated to "BOMAG") as alkylation cocatalyst for the copolymerization of ethylene and butadiene. Each catalytic system 3 was prepared by carrying out a prior activation of the complex 3 by the cocatalyst "BOMAG" according to an Mg cocatalyst/Nd complex molar ratio equal to 5, the activation time being 15 min for all the tests 7-1 to 7-5.

The polymerizations took place in a 250 ml glass reactor, in 200 ml of toluene at a temperature of 80° C. and at a starting pressure of 4 bar or 2 bar in the case of the test 6-5. The monomers were introduced into the medium in the form of gas mixtures comprising 10, 20 and 30% of butadiene.

After a reaction time t (min), the polymerization is halted by cooling and degassing the reactor and then the copolymer is obtained by precipitation from methanol. After drying, a weight w (g) of polymer is obtained.

TABLE 7

Polymerization conditions (complex 3)

| Tests | Complex in mg | [Complex] in µmol·l$^{-1}$ | [Mg] in µmol·l$^{-1}$ | % Bd feed | Final p in bar | Weight of copolymer w in g | Polym. time |
|---|---|---|---|---|---|---|---|
| 7-1 | 50.0 | 247 | 1235 | 30 | 2.8 | 7.61 | 4h 00 |
| 7-2 | 49.6 | 246 | 1230 | 30 | 2.7 | 7.66 | 4h 00 |
| 7-3 | 54.4 | 269 | 1345 | 20 | 4 | 9.74 | 2h 10 |
| 7-4 | 51.8 | 256 | 1280 | 10 | 4 | 9.19 | 1h 40 |
| 7-5 | 55.0 | 272 | 1370 | 10 | 2 | 8.90 | 6h 20 |

TABLE 8

Activities of the complex 3 and macrostructure of the copolymers

| Tests | Activity in g·mol$^{-1}$·h$^{-1}$ | Activity in g·g$^{-1}$·h$^{-1}$ | Mn in g·mol$^{-1}$ | PI | Tg in ° C. |
|---|---|---|---|---|---|
| 7-1 | 38 400 | 38 | 31 600 | 1.69 | −28.3 |
| 7-2 | 38 900 | 39 | 29 550 | 1.50 | −28.2 |
| 7-3 | 83 300 | 82 | 26 950 | 1.52 | −35.7 |
| 7-4 | 107 300 | 106 | 11 885 | 1.65 | −33.6 |
| 7-5 | 25 750 | 26 | 1 600 | 1.56 | — |

TABLE 9

$^{13}$C NMR characterization of the microstructure of the copolymers

| Tests | Molar % Bd units in feed | Molar %Bd units in copolymer | Mol. % 1,4-trans links | Mol. % 12 links | Mol. % T-1,2-Cy links | Mol. % C-1,2-Cy links | Mol. % 1,4-Cy links |
|---|---|---|---|---|---|---|---|
| 7-1 | 30 | 32.1 | 21.5 | 57.5 | 19.0 | 1.9 | * |
| 7-3 | 20 | 21.6 | 19.2 | 32.8 | 34.3 | 4.2 | 9.6 |
| 7-4 | 10 | 12.8 | 17.5 | 20.2 | 41.9 | 5.5 | 14.7 |
| 7-5 | 10 | 10.2 | 25.4 | 7.6 | 45.9 | 5.2 | 15.9 |

*The 1,4-αCy signal could not be integrated due to its low intensity and the superimposition of new small signals. It can be estimated that the level of the 1,4-cyclohexane units represents less than 5% of the butadiene units inserted.

In Table 9:

T-1,2-Cy means trans-1,2-cyclohexane units in the copolymer chain

C-1,2-Cy means cis-1,2-cyclohexane units in the copolymer chain 1,4-Cy means 1,4-cyclohexane units in the copolymer chain.

The copolymer obtained using the complex 3 exhibits units resulting from butadiene comprising links in the form of 1,4-cyclohexane and 1,2-cyclohexane.

ANNEX 1

Analysis of the Lanthanide Borohydride Metallocene Complex According to the Invention by the X-Ray Diffraction Technique The analysis by X-ray diffraction was carried out on a diffractometer using an MoKα source provided with a graphite monochromator (wavelength equal to 0.71069 Å) at a temperature of 150 K.

The crystals of the sample were transferred, in a glovebox under an argon atmosphere, into a small petri dish and covered with Paratone-N (Hampton Research). A small fragment was subsequently cut out and analysed using a "KappaCCD" diffractometer from "Bruker AXS". The intensities diffracted were measured at 150 K with the "Collect" software with Φ and ω scanning at the Kα wavelength of molybdenum. The images obtained were integrated and the intensities were scaled with the "Denzo-SMN" program package.

The structure was resolved by direct methods:

with the "SIR97" program, cf. the paper by A. Altomare, M. C. Burla, M. Camalli, G. Cascarano, C. Giacovazzo, A. Guagliardi, A. G. G. Moliterni, G. Polidori and R. Spagna, "SIR97, An integrated package of computer programs for the solution and refinement of crystal structures using single crystal data", and by least-squares refinement, with the "SHELXL" program, cf. the paper by G. M. Sheldrick: SHELXL-97, Universitat Gottingen, Gottingen, Germany, 1997.

The crystallographic data are summarized in the following table.

| Crystallographic data of the lanthanide borohydride metallocene complex 1: | |
|---|---|
| Molecular formula | C$_{32}$H$_{38}$B$_2$LiNdOSi |
| Molecular weight | 639.51 g/mol |
| Crystal faces | Orange block |
| Dimensions of the crystals (mm) | 0.22 × 0.22 × 0.18 |
| Crystal system | Monoclinic |
| Space group | P2$_1$/c |

-continued

| Crystallographic data of the lanthanide borohydride metallocene complex 1: | |
|---|---|
| a(Å) | 10.4230(10) |
| b(Å) | 14.5290(10) |
| c(Å) | 19.5760(10) |
| α(°) | 90.00 |
| β(°) | 100.8500(10) |
| γ(°) | 90.00 |
| V(Å³) | 2911.5(4) |
| Z | 4 |
| d(g·cm⁻³) | 1.459 |
| F(000) | 1300 |
| μ(cm⁻¹) | 1.848 |
| Absorption corrections | Multiscanning; 0.6866 min, 0.7321 max |
| Diffractometer used | "KappaCCD" |
| X-ray source | MoKα |
| λ(Å) | 0.71069 |
| Monochromator | Graphite |
| T (K) | 150.0(1) |
| Scanning mode | Phi and omega scans |
| θ maximum | 30.02 |
| "HKL" ranges | −14 14; −18 20; −27 27 |
| Reflections measured | 13551 |
| Unique data | 8443 |
| "Rint" | 0.0192 |
| Reflections used | 6770 |
| Criterion | I > 2σI |
| Type of refinement | Fsqd |
| Hydrogen atoms | Mixtures |
| Refined parameters | 373 |
| Reflections/parameters | 18 |
| wR2 | 0.0841 |
| R1 | 0.0317 |
| Weights a, b | 0.0454; 0.0000 |
| GoF | 1.033 |
| Difference peak/hole (e Å⁻³) | 1.747(0.094)/−0.901(0.094) |

ANNEX 2

Analysis by Steric Exclusion Chromatography of the Copolymers a) For the copolymers which are soluble at ambient temperature in tetrahydrofuran (THF), the molar masses were determined by steric exclusion chromatography in THF. The samples were injected using a "Waters 717" injector and a "Waters 515 HPLC" pump at a flow rate of 1 ml·min⁻¹ into a series of "Polymer Laboratories" columns.

This series of columns, placed in a chamber thermostatically controlled at 45° C., is composed of:
1 precolumn: PL Gel 5 μm,
2 columns: PL Gel 5 μm Mixed C,
1 column: PL Gel 5 μm 500 Å.

Detection was carried out using a "Waters 410" refractometer.

The molar masses were determined by relative calibration using polystyrene standards certified by "Polymer Laboratories".

Without being an absolute method, SEC makes it possible to understand the distribution of the molecular weights of a polymer. Starting from commercial products which are standards, the different number-average molecular weights (Mn) and weight-average molecular weights (Mw) can be determined and the polydispersity index calculated (PI=Mw/Mn).

b) For the copolymers which are insoluble at ambient temperature in tetrahydrofuran, the molar masses were determined in 1,2,4-trichlorobenzene. They were first of all dissolved under hot conditions (4 h 00 at 150° C.) and were then injected at 150° C. with a flow rate of 1 ml·min into a "Waters Alliance GPCV 2000" chromatograph equipped with three "Styragel" columns (2 "HT6E" columns and 1 "HT2" column).

Detection was carried out using a "Waters" refractometer.

The molar masses were determined by relative calibration using polystyrene standards certified by "Polymer Laboratories".

ANNEX 3

¹H and ¹³C NMR Determination of the Microstructure of the Butadiene Units Inserted into the Copolymers of Ethylene and Butadiene

High-resolution NMR spectroscopic analysis was carried out with a Bruker DRX 400 spectrometer at frequencies of 400 MHz for observation of ¹H and 100.6 MHz for observation of ¹³C. The 1D spectra were obtained with a 5-mm QNP probe at a temperature of 363 K. For the 2D spectra, use was made of a broadband probe with a field gradient along the z axis. The ¹H-¹H correlations were determined with a COSY-GS sequence and the ¹H-¹³C correlations with the HMQC-GS and HMBC-GS sequences. A mixture of tetrachloroethylene (TCE) and perdeuterobenzene (C6D6) (ratio 2/1 by volume) was used as solvent. The concentrations of polymer for the analysis are between 10 and 15% (w/w). The chemical shifts (δ) are given in ppm using tetramethylsilane (TMS) as internal reference; in the absence of TMS, the resonance of polyethylene ("PE" at δ=30.06 ppm) is used as internal reference.

NOTATIONS

The following symbols have been used in all the schemes and tables of this annex:
T: butadiene or isoprene unit inserted as trans-1,4,
C: butadiene or isoprene unit inserted as cis-1,4,
L: butadiene unit inserted as cis- or trans-1,4,
V: butadiene unit inserted as 1,2(vinyl),
E: ethylene unit,
B: butadiene unit (without distinction in microstructure),
T-1,2-Cy: trans-1,2-cyclohexane unit,
C-1,2-Cy: cis-1,2-cyclohexane unit,
1,4-Cy: 1,4-cyclohexane unit.

As concerns the assignment of the signals resulting from the 1,2 (V) and trans-1,4 (T) butadiene units and the trans-1,2-cyclohexane (T-1,2-Cy) units, reference should be made to the paper "Investigation of Ethylene/Butadiene Copolymers Microstructure by ¹H and ¹³C NMR": M. F. Llauro, C. Monnet, F. Barbotin, V. Monteil, R. Spitz, C. Boisson, Macromolecules, 2001, 34, 6304.

Scheme 1: notations employed to denote the various carbons of a 1,2-cyclohexane unit in the form isolated in the copolymer chain.

TABLE 1

Chemical shifts of the carbons relating to the trans-1,2-cyclohexane units

| Type of carbon | δ (ppm) |
| --- | --- |
| T-1,2-αCy | 33.96 |
| T-1,2-βCy | 27.00 |
| T-1,2-γCy | 30.59 |
| T-1,2-α'Cy | 32.26 |
| T-1,2-β'Cy | 26.66 |
| T-1,2-(CH)Cy | 42.01 |

TABLE 2

Chemical shifts of the carbons relating to the cis-1,2-cyclohexane units

| Type of carbon | δ (ppm) |
| --- | --- |
| C-1,2-αCy | 28.14 |
| C-1,2-βCy | 29.25 |
| C-1,2-γCy | |
| C-1,2-α'Cy | 30.50 |
| C-1,2-β'Cy | 24.22 |
| C-1,2-(CH)Cy | 39.67 |

Scheme 2: notations employed to denote the various carbons of a 1,4-cyclohexane unit in the form isolated in the copolymer chain.

TABLE 3

Chemical shifts of the carbons relating to the 1,4-cyclohexane units

| Type of carbon | δ (ppm) |
| --- | --- |
| 1,4-αCy | 37.90 |
| 1,4-βCy | 27.30 |
| 1,4-γCy | 30.40 |
| 1,4-α'Cy | 33.90 |
| 1,4-(CH)Cy | 38.40 |

| Crystallographic data of the complex 3 | |
| --- | --- |
| Molecular formula | $C_{56}H_{86}B_2LiNdO_3Si$ |
| Molecular weight | 1008.18 g/mol |
| Crystal faces | Yellow block |
| Dimensions of the crystals (mm) | 0.20 × 0.18 × 0.15 |
| Crystal system | Triclinic |
| Space group | P-1 |
| a(Å) | 16.5340(10) |
| b(Å) | 18.0490(10) |
| c(Å) | 21.2150(10) |
| α(°) | 75.0600(10) |
| β(°) | 71.0500(10) |
| γ(°) | 71.2000(10) |
| V(Å³) | 5584.9(5) |
| Z | 4 |
| d(g·cm⁻³) | 1.189 |
| F(000) | 2100 |
| μ(cm-1) | 0.990 |
| Absorption corrections | Multiscanning; 0.8267 min, 0.8658 max |
| Diffractometer used | KappaCCD |
| X-ray source | MoKα |
| λ(Å) | 0.71069 |
| Monochromator | Graphite |
| T (K) | 150.0(1) |
| Scanning mode | Phi and omega scans |
| θ maximum | 27.48 |
| "HKL" ranges | −21 19; −23 22; −27 22 |
| Reflections measured | 41244 |
| Unique data | 21641 |
| "Rint" | 0.0174 |
| Reflections used | 14863 |
| Criterion | I > 2σI) |
| Type of refinement | Fsqd |
| Hydrogen atoms | Mixed |
| Refined parameters | 1025 |
| Reflections/parameters | 14 |
| wR2 | 0.2107 |
| R1 | 0.0656 |
| Weights a, b | 0.0961; 36.570 |
| GoF | 1.024 |
| Difference peak/hole (e Å⁻³) | 5.506(0.147)/−3.370(0.147) |

The invention claimed is:

1. A copolymer of ethylene and butadiene, that exhibits both:
    a molar level of units resulting from butadiene which is equal to or greater than 25%, and
    a molar level of 1,2-cyclohexane links in the units resulting from butadiene which is equal to or greater than 25%.

2. A copolymer of ethylene and butadiene according to claim 1, that exhibits a number-average molecular weight Mn equal to or greater than 30 000 g/mol.

3. A copolymer of ethylene and butadiene obtained according to claim 1, that exhibits units resulting from butadiene comprising links in the form of 1,4-cyclohexane.

* * * * *